(12) United States Patent
Bremer et al.

(10) Patent No.: US 6,447,575 B2
(45) Date of Patent: Sep. 10, 2002

(54) METHOD AND APPARATUS FOR GAS CHROMATOGRAPHY ANALYSIS OF SAMPLES

(75) Inventors: Ralf Bremer, Oberhausen; Andreas Hoffmann, Duisburg, both of (DE)

(73) Assignee: Gertstel Systemtechnik GmbH & Co., Mulheim (DE)

(*) Notice: Subject to any disclaimer, the term of this patent is extended or adjusted under 35 U.S.C. 154(b) by 5 days.

(21) Appl. No.: 09/738,543

(22) Filed: Dec. 15, 2000

(30) Foreign Application Priority Data

Dec. 16, 1999 (DE) .......................... 199 60 631.5

(51) Int. Cl.[7] .............................................. B01D 15/08
(52) U.S. Cl. .................................. 95/86; 95/87; 96/104
(58) Field of Search .............................. 95/82, 86, 87, 95/89; 96/101, 104–106

(56) References Cited

U.S. PATENT DOCUMENTS

| | | | | |
|---|---|---|---|---|
| 3,225,521 A | * | 12/1965 | Burow | 95/86 |
| 4,274,967 A | * | 6/1981 | Snyder | 95/86 X |
| 4,849,179 A | * | 7/1989 | Reinhardt et al. | 95/89 X |
| 4,948,389 A | * | 8/1990 | Klein et al. | 95/87 X |
| 5,049,509 A | * | 9/1991 | Szakasits et al. | 96/101 X |
| 5,152,176 A | * | 10/1992 | Bryselbout et al. | 95/86 X |
| 5,281,256 A | * | 1/1994 | Sacks et al. | 95/86 |
| 5,588,988 A | * | 12/1996 | Gerstel et al. | 96/101 |
| 5,596,876 A | * | 1/1997 | Manura et al. | 95/87 X |

FOREIGN PATENT DOCUMENTS

JP 01-305352 A * 12/1989 .................... 95/82

* cited by examiner

Primary Examiner—Robert H. Spitzer
(74) Attorney, Agent, or Firm—Townsend and Townsend and Crew LLP

(57) ABSTRACT

The invention relates to gas chromatography analysis of a sample having components to be investigated and water contained therein, which after thermodesorption is separated and analyzed, the thermodesorbed sample being transferred by a carrier gas into a first polar separation column which retains higher-boiling components and water and passes low-boiling components, the latter being led, past a branching point which leads, on the one hand, to a second polar or non-polar separation column and, on the other hand, to the non-polar separation column, to the non-polar separation column in a fashion excluding access to the second polar or non-polar separation column, after which higher-boiling components and water are transferred to the second polar or non-polar separation column in a fashion excluding access to the non-polar separation column, water being eliminated upstream of the second polar or non-polar separation column by cryofocussing.

34 Claims, 3 Drawing Sheets

METHOD AND APPARATUS FOR GAS CHROMATOGRAPHY ANALYSIS OF SAMPLES

FIELD OF THE INVENTION

The invention relates to a method and apparatus for gas chromatography analysis of samples.

To use gas chromatography to investigate small quantities of components present in gases or liquids, such as foreign substances or pollutants or impurities, it is known firstly to enrich these in order then to feed them into a gas chromatograph via an appropriate feeding system. However, problems occur in this case when the collected samples contain moisture such as is the case, for example, when pollutants contained in the air are enriched, since the moisture contained in the air is then also enriched.

However, water severely disturbs a gas chromatography system, and likewise the analysis, in the case of which, for example, a substantial loss in sensitivity occurs in the mass spectrometer. The presence of water in separation columns alters the retention time, doing so, specifically, as a function of quantity and differently for different substances, thus creating the need to eliminate this as completely as possible in order to obtain reliable measurement results.

BACKGROUND OF THE INVENTION

It is known to eliminate the moisture which is present in samples to be chromatographically analyzed by osmosis. However, this has the disadvantage that polar components are also eliminated in the process, while non-polar components remain essentially uninfluenced. However, the elimination of polar components other than water falsifies the chromatogram.

Also known are packed capillary columns which exhibit a temperature-dependent adsorptivity with reference to water, so that given appropriate setting, low-boiling components are passed while higher-boiling components and water are retained.

SUMMARY OF THE INVENTION

It is an object of the invention to provide a method for gas chromatography analysis of samples which permits reliable gas chromatograms to be obtained from samples containing water.

It is a further object of the invention to provide an apparatus for gas chromatography analysis of samples which permits reliable gas chromatograms to be obtained from samples containing water.

According to the invention a method for gas chromatography analysis of a sample after preceding thermodesorption, in which the components to be separated and water are contained, is provided, wherein the thermodesorbed sample is transferred by means of carrier gas into a first polar separation column which retains higher-boiling components and water and passes low-boiling components, said low boiling components being led, past a branching device which leads, on the one hand, to a second polar or non-polar separation column and, on the other hand, to a non-polar separation column, to the non-polar separation column in a fashion excluding access to the second polar or non-polar separation column, after which the higher-boiling components and the water are lead to the second polar or non-polar separation column in a manner excluding access to the non-polar separation column, the water being eliminated upstream of the second polar or non-polar separation column by means of cryofocussing.

According to the invention, further an apparatus for gas chromatography analysis of a sample is provided, comprising:

a thermodesorption device for holding a sampling tube;

a first polar separation column being connected downstream of the thermodesorption device;

a branching device being connected downstream of the first polar separation column;

a non-polar separation column;

a second separation column being of the group of a polar and a non-polar separation column;

wherein said branching device being switchable over between said non-polar separation column; and a device for eliminating water which is connected upstream of the second separation column.

By virtue of the fact that according to the present invention use is made as a precolumn of a polar separation column with a stationary phase, which water does not initially have the effect of separating it preliminarily into two fractions, higher-boiling components and water can be retained at the beginning, while low-boiling components are passed. The low-boiling components are separated on the non-polar separation column via a pneumatically closeable bifurcation which leads, on the one hand, to a non-polar separation column for gases and, on the other hand, via a cryofocussing device, to a further polar or non-polar separation column, whereupon after pneumatically switching over the bifurcation the water with higher-boiling components is eliminated in the region of the cryofocussing device, whereupon the higher-boiling components are separated in the polar or non-polar separation column downstream of the cryofocussing device. In addition, in this case the water elimination with subsequent separation and analysis of a sample, and the separation on the further separation column with subsequent analysis of another sample, can be carried out simultaneously.

In this case, not only gaseous but also liquid samples which contain water can be taken automatically by means of the apparatus.

Further objects, embodiments and advantages of the invention will become apparent from the following description and the claims.

BRIEF DESCRIPTION OF THE DRAWINGS

The invention is explained below in more detail with reference to preferred embodiment illustrated schematically in the attached illustrations.

DETAILED DESCRIPTION OF THE PREFERRED EMBODIMENT

Figure 1:
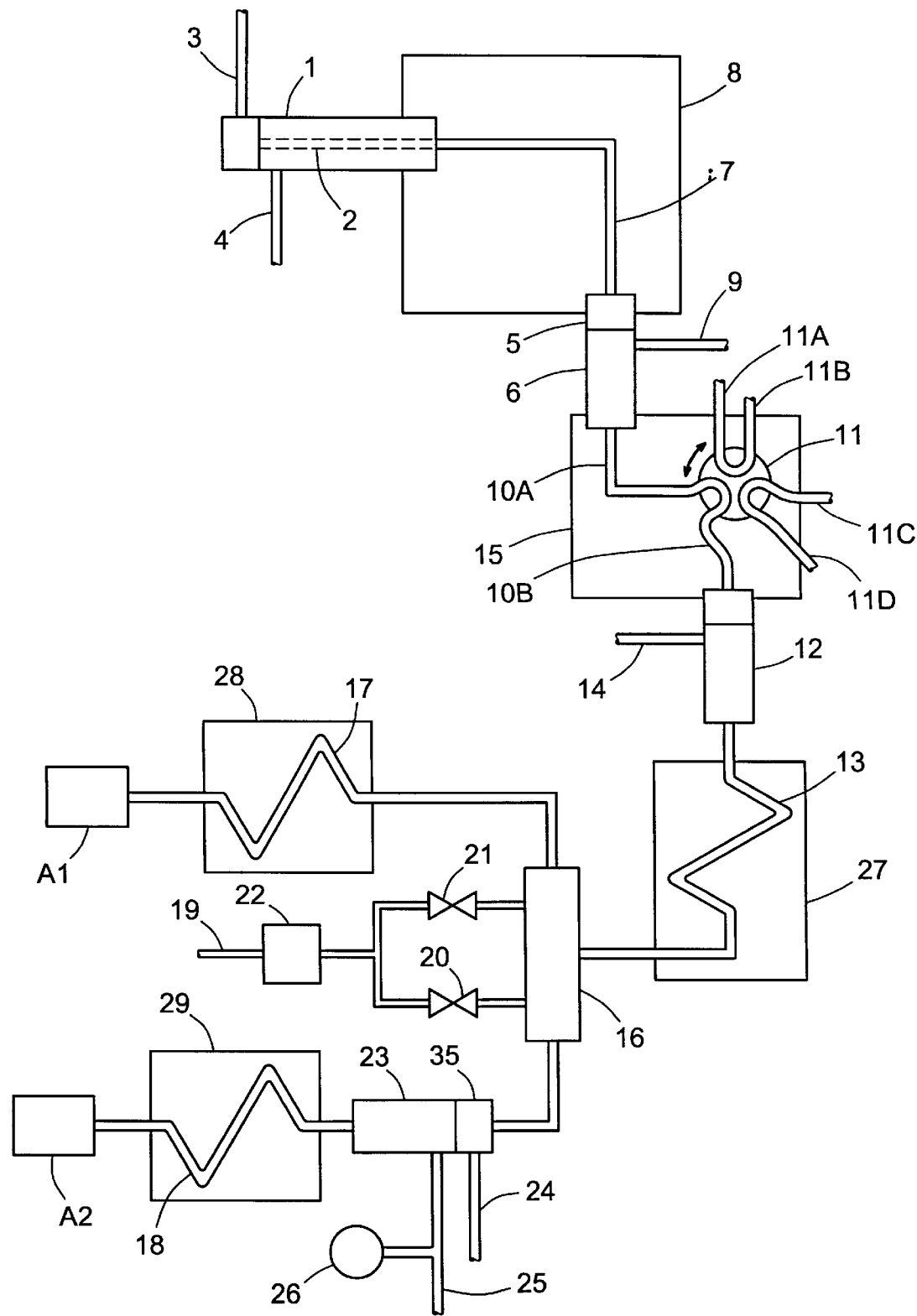
FIG. 1 shows a diagram of a gas chromatography apparatus according to the invention, partially in section.

The gas chromatography apparatus illustrated in FIG. 1 comprises a thermodesorption device 1 for a sample contained in a sampling tube 2, a carrier gas connection 3 and a gas exhaust line 4 being provided. A transfer capillary 7 leading from the thermodesorption device 1 to a feed head 5 of a cryofocussing device 6 can be heated by a transfer furnace 8 in order to avoid material losses upon transfer from the sampling tube 2 to the cryofocussing device 6. The cryofocussing device 6 comprises a gas exhaust line 9. A transfer capillary 10a, 10b downstream of the cryofocussing device 6 leads, if appropriate, via a switchover valve 11 to a column collecting piece 12 of a polar separation column 13 serving as capillary precolumn, the column connecting piece 12 comprising a gas exhaust line 14. The switchover valve 11 also comprises several feed or discharge lines 11a–11d for flushing, calibration or automatic sampling. The transfer capillary 10a, 10b is arranged in a transfer furnace 15 which can, if appropriate, form a common furnace with the transfer furnace 8.

A branching device 16 is arranged at the end downstream of the polar separation column 13, which exhibits stable properties with regard to separation in the presence of water. Separation columns 17,18 are connected separately from one another to the branching device 16, it being possible to exclude pneumatically the access to in each case one of the separation columns 17,18 via a gas line 19, which can be charged with gas via a valve 20 or 21 and a controller 22.

The separation column 17 is a non-polar separation column which, in particular, operates according to the principle of a micropacked column, and serves to separate low-boiling components. The separation column 17 is connected to an analyzer A1.

The separation column 18 is a polar or non-polar separation column with stable properties with regard to the separation of polar components. The separation column 18 is connected to an analyser A2. Connected upstream of the separation column 18 is a device 23 for eliminating water, which comprises a carrier gas connection 24 and a gas exhaust line 25 for the purpose of eliminating interfering water. In this case, a thermal conductivity detector 26 connected to the gas exhaust line 25 is used to monitor the completeness of the elimination.

The polar separation column 13 can be arranged in a furnace 27 which can, if appropriate, form a single furnace with the transfer furnace 8.

The capillary separation columns 17,18 are preferably arranged in the furnaces 28 and 29, respectively, but they can also be arranged in a common furnace, if appropriate together with the polar separation column 13.

Figure 2:
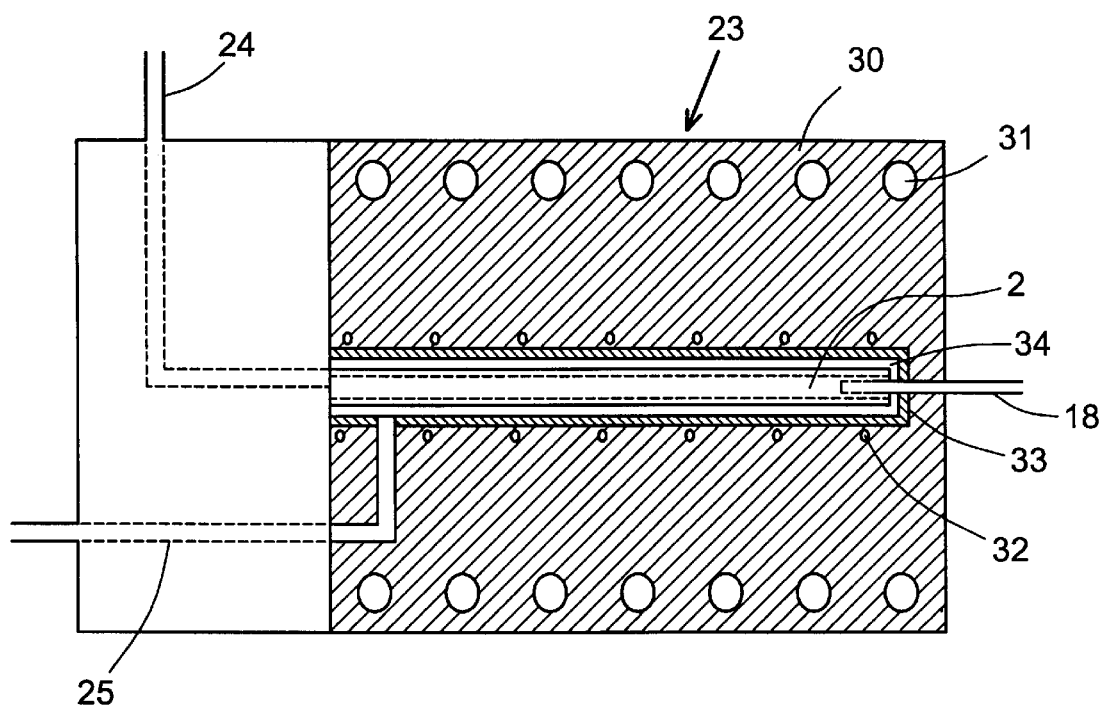
FIG. 2 shows the diagrammatic design of an embodiment of a thermodesorption device or cryofocussing device or a device for eliminating water for the gas chromatography device of FIG. 1, in section.

The device 23, illustrated in FIG. 2, for eliminating water comprises a cooling device, which can be formed by a Peltier element, a cyrostat or a passage for liquefied gas such as liquid nitrogen. In the exemplary embodiment illustrated, a housing casing 30 is provided with coolant bores 31 which can be connected to a coolant source, the housing casing 30 accommodating a metal tube 33 which is surrounded by a heating winding 32 and for its part accommodates the sampling tube 2. An annular gap 34 which is connected to the gas exhaust line 25 is located between the metal tube 33 and the sampling tube 2. The carrier gas connection 24 opens into the sampling tube 2 in the region of a feed head 35. The separation column 18 is plugged into the device 23 for eliminating water in such a way that it projects into the sampling tube 2. Since the inside diameter of the sampling tube 2 is larger than the outside diameter of the separation column 18, the interior of the sampling tube 2 is also connected to the annular gap 34.

The thermodesorption device 1 and the cryofocussing device 6 can be designed in a fashion corresponding to the device 23 for eliminating water, and so reference is made to FIG. 2 in each case in connection with these devices. The design can be selected, for example, to accord with DE 44 19 596 C1, but it is also possible here to provide cooling by a Peltier element or a cryostat, while consideration may be given respectively in this connection to a heating cartridge for example in accordance with DE 198 17 017 A1. However, if appropriate, the annular gap 34 and the gas exhaust line 4 or 9 can be dispensed with, if appropriate, in the case of the thermodesorption device 1 and the cryofocussing device 6 when split-mode operation is not desired. The thermodesorption device 1 can be designed as in the case where sampling tubes 2 are to be used such as described, for example, in DE 195 20 715 C1. Each of DE 44 19 596 C1, DE 198 17 017 A1, and DE 195 20 715 C1 is incorporated herein by reference, as are any English-language equivalents thereof.

Figure 3:
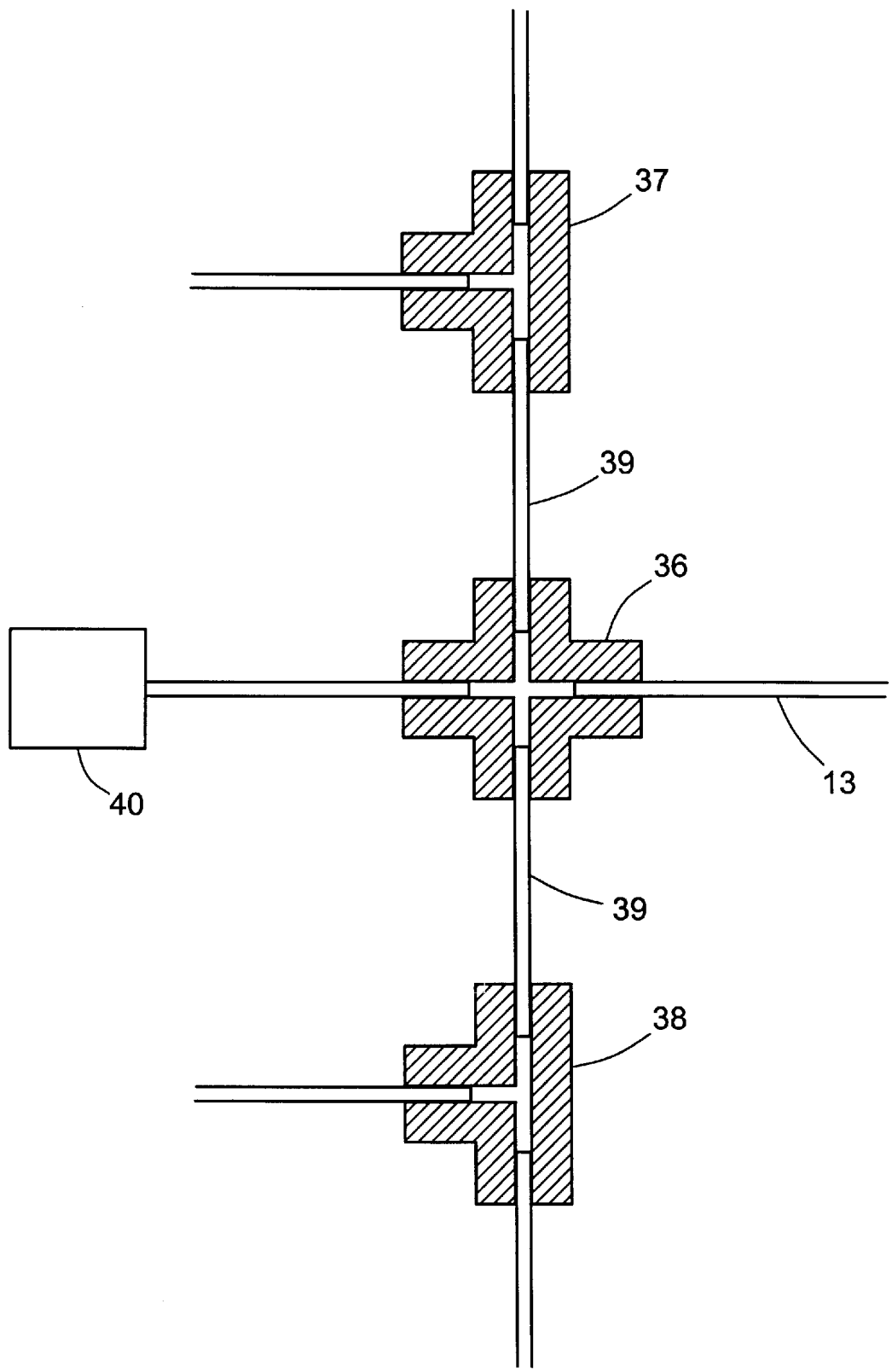
FIG. 3 shows a diagram of a design of a branching point for the gas chromatography device of FIG. 1, in section.

In the embodiment of the branching device 16 of FIG. 3, a central branching piece 36 is connected to two further branching pieces 37,38 via capillary adapters 39 which, for their part, are connected via the valve 20 or 21 and the controller 22 to the gas line 19 or to the separation column 17 or 18, it being possible, if appropriate, to connect the central branching piece 36 to a monitor detector 40, in particular a thermal conductivity detector.

A sample contained in the sampling tube 2 is thermodesorbed in the thermodesorption device 1 by controlled heating of the sampling tube 2 by means of the heating winding 32. During thermodesorption, carrier gas is fed into the sampling tube 2 via the carrier gas connection 3, and led into the cryofocussing device 6 via the heated transfer capillary 7 for the purpose of transporting desorbed substances, including water which is present. Uniform feeding of carrier gas is maintained constant in this case in each method step via a flow sensor with a controller. Since thermodesorption is performed without splitting, the gas exhaust line 4 remains closed and thereby pneumatically closes the access to the annular gap 34.

Initially, the cryofocussing device 6 is closed off at the end, if appropriate by means of the switchover valve 11, from the column connecting piece 12, its gas exhaust line 9 is opened, for example via a valve (not illustrated), and its sampling tube 2 is cooled down to minus 150° C. by appropriate cooling, for example with liquid nitrogen, such that all the components of the sample which are to be investigated, including the water contained, are collected in the sampling tube 2 and thus enriched. Thereafter, the gas exhaust line 9 is closed, while the sampling tube 2 is heated up, while being monitored, to a temperature of, for example, 350° C., by means of the heating winding 32, all the enriched components leaving the sampling tube 2 of the cryofocussing device 6 and now being led into the separation column 13 by means of carrier gas because of the open switchover valve 11 via the column connecting piece 12.

The preliminary separation into two fractions of the separation column 13 is initially not influenced by water which is present, and higher-boiling components and water are retained there by interaction forces of different strength for a longer time than low-boiling, essentially non-polar components.

In the first phase of the separation by the polar separation column 13 in which the furnace 27 is at ambient temperature, the low-boiling non-polar components, i.e. those with one to approximately four or more carbon atoms, flow through the polar separation column 13 virtually without a separation effect, and subsequently through the branching device 16. The valve 20 is opened in this case, and so the branching device 16 is pneumatically closed towards the polar or non-polar separation column 18, and the low-boiling non-polar components are permitted to pass to the non-polar separation column 17 by means of a controlled carrier gas flow. These components are separated in the non-polar separation column 17 and analyzed in the analyzer A1.

In a second phase of the separation by the polar separation column 13, the valve 20 is closed and the valve 21 is opened such that the branching device 16 is now pneumatically closed off from the non-polar separation column 17. The valves 20,21 are switched over in principle as a function of time, the switch over being calibrated to a retention time of a specific compound, which is low boiling by comparison with water, in the non-polar separation column 17, for example to the retention time of toluene, but it can also be performed earlier, if appropriate, when the monitor detector 40 which reacts to water outputs a signal on the basis of incoming water which has the effect of permitting access by higher-boiling components and water on the basis of the now reversed direction of the overall gas flow to the polar separation column 18 via the device 33 for eliminating water, the polar separation column 13 then being additionally heated via the furnace 27 in order to release all higher-boiling components and/or water.

The device 23 for eliminating water permits higher-boiling components to be separated from water in three phases.

In a first phase, the cryofocussing, the higher-boiling components and water are collected and enriched—as in the case of enrichment in the cryofocussing device 6. In a second phase, the sampling tube 2 of the device 23 for eliminating water is heated by means of its heating winding 32, the water being eliminated via the open gas exhaust line 25. This heating is performed to a temperature above the freezing point of water and below the boiling point of water, preferably to a relatively low temperature of, for example, 10 to 20° C., this temperature being selected in such a way that as little loss of components as possible results in this case, but an adequate water vapor partial pressure is present. The monitoring of the water content in the sample is performed in this case by means of the thermal conductivity detector 26, which reacts to the presence of water and is connected to the gas exhaust line 25. Once the water has been completely eliminated, the gas exhaust line 25 is closed on the basis of a signal output by the thermal conductivity detector 26, whereupon in the third phase the sampling tube 2 of the device 23 for eliminating water is heated further in a programmed fashion by means of the heating winding 32, and the individual components are released again one after another and are then led into the polar or non-polar separation column 18 in which they are successively separated and analyzed in the analyzer A2.

Water is eliminated in the device 23 for eliminating water by virtue of the fact that its sampling tube 2 is heated by means of the heating winding 32, and that, with the gas exhaust line 25 open, the carrier gas flowing past a fed sample containing water flows to the polar or non-polar separation column 18 at the end, averted from the feed head 35, of the sampling tube 2 of the device 23 for eliminating water, back to the gas exhaust line 25 through the annular gap 34, and is thereby eliminated. This form of elimination of individual components, also termed split-mode operation, can also take place in the cryofocussing device 6 by means of a gas exhaust line 9, which is open here, and in the thermodesorption device 1 by means of a gas exhaust line 4, which is open here. The gas exhaust lines 4,9 and 25 each have a valve which is opened, preferably pneumatically, by means of pressure control during split-mode operation.

It is expedient for the sample to be introduced quickly in the column connecting piece 12 on the basis of operation as a consequence of a continuously open gas exhaust line 14 by means of the flow velocity, thereby increased, in order in this way to achieve a defined peak end (avoidance of peak tailing) with a defined sharpness of separation. Thinning of the sample resulting therefrom is generally acceptable.

A sample can be introduced into the thermodesorption device 1 by means of an exchangeable sampling tube 2. Instead of this, the sample can, however, also be collected in the sampling tube 2 of the thermodesorption device 1 by the sucked-in ambient atmosphere during split-mode operation with the gas exhaust line 9 open, the gas being eliminated via the annular gap 34 and the gas exhaust line 9. If appropriate, the switchover valve 11 can, also be arranged upstream of the cryofocussing device 6 in the region of the transfer capillary 7.

The switchover valve 11 is adjusted after a passage of the sample in such a way that firstly, with the aid of the now connected feed line 11a and 11b the sample inlet is flushed up to the outlet, and secondly, with the aid of the likewise connected transfer capillary 10a, the feed line 11a and 11b, and also the connected feed line to the carrier gas connection 3, the thermodesorption device 1 and the cryofocussing device 6 are flushed, while because of the closed exhaust line 14 the sample is led further to the column interface 12 via the polar separation column 13. Consequently, on the basis of the above circuit it is possible to take a new sample in parallel with the sample to be analyzed or to carry out a calibration of the thermodesorption device 1 and of the cryofocussing device 6.

In a preferred embodiment, the separation columns 13,17 and 18 are likewise arranged in individual furnaces 27,28 and 29 such that after passage of the respective sample the separation columns 13,17,18 are cooled down individually and prepared for the subsequent sample, the temperature intervals being selected to be smaller by the furnace 27,28, 29, which is to be assigned respectively to only one separation column 13,17,18, and cooling taking place more quickly.

The pneumatic exclusion from the polar or non-polar separation column 18 via the device 23 for eliminating water, or from the non-polar separation column 17 is achieved on the basis of switching over the valves 20,21 and on the basis of the controller 22, which sets a higher flow velocity of the gas from the gas line 19 than is prescribed by the carrier gas flow which flows through the polar separation column 13. The capillary adapters 39, which have a diameter of 50 $\mu$m to 100 $\mu$m, for example, are to be dimensioned in this case in terms of length and diameter and as a function of the gas pressure used in such a way that no diffusion takes place from the central branching piece 36 up to that one of the two branching pieces 37,38 which leads to the separation column 17,18 respectively not to be used.

While the invention has been shown and described with reference to a preferred embodiment, it should be apparent to one of ordinary skill in the art that many changes and modifications may be made without departing from the spirit and scope of the invention as defined in the claims.

What is claimed is:

1. A method for gas chromatography analysis of a sample after preceding thermodesorption, in which the components to be separated and water are contained, wherein the thermodesorbed sample is transferred by means of carrier gas into a first polar separation column which retains higher-boiling components and water and passes low-boiling components, said low boiling components being led, past a branching device which leads, on the one hand, to a second separation column of the group of a non-polar and a polar separation column and, on the other hand, to a third non-polar separation column, to the third non-polar separation column in a manner excluding access to the second separation column, after which the higher-boiling components and the water are lead to the second separation column in a manner excluding access to the third non-polar separation column, the water being eliminated upstream of the second separation column by means of cryofocussing.

2. The method of claim 1, wherein the sample is cryofocussed subsequently to the thermodesorption before it is transferred into the first polar separation column.

3. The method of claim 1, wherein the sample is thermodesorbed when located in an exchangeable sampling tube.

4. The method of claim 3, wherein the sample in the sampling tube is collected in a thermodesorption device by leading through an appropriate medium flow.

5. The method of claim 1, wherein the access to the third non-polar and to the second separation column is pneumatically excluded.

6. The method of claim 1, wherein the access is switched over as a function of time from the third non-polar to the second separation column.

7. The method of claim 1, wherein the access is switched over from the third non-polar to the second separation column as a function of a signal calibrated to a retention time of a compound with a lower retention time than water.

8. The method of claim 7, wherein the signal is calibrated to the retention time of toluene.

9. The method of claim 1, wherein the access is switched over from the third non-polar to the second separation column on the basis of a detected water breakthrough at the first polar separation column.

10. The method of claim 1, wherein furnaces for the third non-polar and the second separation column are operated independently of one another.

11. The method of claim 1, wherein the sample is imparted an increased rate of flow upstream of the access to the first polar separation column.

12. An apparatus for gas chromatography analysis of a sample, comprising:
a thermodesorption device for holding a sampling tube;
a first polar separation column being connected downstream of the thermodesorption device;
a branching device being connected downstream of the first polar separation column;
a non-polar separation column;
a second separation column being of the group of a polar and a non-polar separation column;
wherein said branching device being switchable over between said non-polar separation column; and
a device for eliminating water which is connected upstream of the second separation column.

13. The apparatus of claim 12, wherein a cryofocussing device is arranged between the thermodesorption device and the first polar separation column.

14. The apparatus of claim 12, wherein the device for eliminating water comprises a cryofocussing device.

15. The apparatus of claim 14, wherein the device for eliminating water comprises a cooling device and a heating device.

16. The apparatus of claim 15, wherein the device for eliminating water accommodates a coolable metal tube which is surrounded by a heating winding and in which a further sampling tube is located, there being arranged between the metal tube and the further sampling tube an annular gap which is connected to a gas exhaust line to which a thermal conductivity detector is connected.

17. The apparatus of claim 12, wherein the thermodesorption device is provided with a coolable metal tube surrounded by a heating winding, the coolable metal tube surrounding the sampling tube.

18. The apparatus of claim 17, further comprising an annular gap between the coolable metal tube and the sampling tube, the annular gap being connected to a gas exhaust line.

19. The apparatus of claim 12, wherein the sampling tube of the thermodesorption device is exchangeable.

20. The apparatus of claim 12, further comprising a switchover valve arranged to isolate the thermodesorption device.

21. The apparatus of claim 12, wherein the device of the group comprising a thermodesorption device and a downstream cryofocussing device is connected to the first polar separation column by means of a transfer capillary.

22. The apparatus of claim 12, wherein a column connecting piece comprising a gas exhaust line is connected upstream of the first polar separation column.

23. The apparatus of claim 12, wherein the branching device comprises a central branching piece and two further branching pieces which are interconnected by means of capillary adapters.

24. The apparatus of claim 23, wherein a monitor detector is connected to the central branching piece.

25. The apparatus of claim 12, wherein a heatable transfer capillary and a further heatable transfer capillary are located in two separate furnaces.

26. The apparatus of claim 12, wherein a heatable transfer capillary and a further heatable transfer capillary are located in a common furnace.

27. The apparatus of claim 12, wherein the first polar separation column is located in a dedicated furnace.

28. The apparatus of claim 12, wherein the first polar separation column is located in the furnace.

29. The apparatus of claim 12, wherein the second separation column and the third separation column are respectively located in a furnace, respectively.

30. The apparatus of claim 12, wherein the second separation column and the third separation column are located in a common furnace.

31. The apparatus of claim 12, wherein the first polar separation column, the second separation column and the third separation column are located in a common furnace.

32. The apparatus of claim 12, further comprising a cryofocussing device holding a sample tube provided with a coolable metal tube surrounded by a heating winding, the coolable metal tube surrounding the sampling tube.

33. The apparatus of claim 32, further comprising an annular gap between the coolable metal tube and the sampling tube, the annular gap being connected to a gas exhaust line.

34. The apparatus of claim 32, further comprising a switchover valve arranged to isolate the cryofocussing device.

* * * * *

UNITED STATES PATENT AND TRADEMARK OFFICE
CERTIFICATE OF CORRECTION

PATENT NO. : 6,447,575 B2
DATED : September 10, 2002
INVENTOR(S) : Bremer et al.

It is certified that error appears in the above-identified patent and that said Letters Patent is hereby corrected as shown below:

<u>Title page,</u>
Item [73], should read as follows:
-- [73] Assginee: Gerstel Systemtechnik GmbH & Co. KG --

Signed and Sealed this

Eighteenth Day of February, 2003

JAMES E. ROGAN
*Director of the United States Patent and Trademark Office*